US008557537B2

(12) United States Patent
Rokbi et al.

(10) Patent No.: US 8,557,537 B2
(45) Date of Patent: *Oct. 15, 2013

(54) METHOD FOR THE PRODUCTION OF OVERPRODUCING *STAPHYLOCOCCUS AUREUS* STRAINS

(75) Inventors: Bachra Rokbi, Lyons (FR); Celine Lafont, Saint Symphorien sur Coise (FR)

(73) Assignee: Sanofi Pasteur SA, Lyons (FR)

( * ) Notice: Subject to any disclaimer, the term of this patent is extended or adjusted under 35 U.S.C. 154(b) by 442 days.

This patent is subject to a terminal disclaimer.

(21) Appl. No.: 12/880,566

(22) Filed: Sep. 13, 2010

(65) Prior Publication Data

US 2010/0330656 A1 Dec. 30, 2010

Related U.S. Application Data

(62) Division of application No. 11/408,729, filed on Apr. 21, 2006, now Pat. No. 7,863,013.

(60) Provisional application No. 60/684,103, filed on May 24, 2005.

(30) Foreign Application Priority Data

Apr. 25, 2005 (FR) .................................. 05 04115

(51) Int. Cl.
*C12Q 1/04* (2006.01)
*C12Q 1/14* (2006.01)

(52) U.S. Cl.
USPC .............................................. 435/34; 435/36

(58) Field of Classification Search
None
See application file for complete search history.

(56) References Cited

U.S. PATENT DOCUMENTS

| 6,045,805 | A | 4/2000 | Moreau |
| 6,984,431 | B2 | 1/2006 | Mass et al. |
| 2007/0031939 | A1 | 2/2007 | Rokbi et al. |

FOREIGN PATENT DOCUMENTS

| WO | 03/061558 A2 | 7/2003 |
| WO | 2004/043407 A2 | 5/2004 |
| WO | 2004/080490 A2 | 9/2004 |
| WO | 2006/114500 A2 | 11/2006 |

OTHER PUBLICATIONS

Hamilton, Carol M., et al., "New Method for Generating Deletions and Gene Replacements in *Escherichia coli*," Journal of Bacteriology, Sep. 1989, pp. 4617-4622, vol. 171, No. 9, American Society for Microbiology.
Sau Subrata et al., "Molecular Characterization ad Transcriptional Analysis of Type 8 Capsule Genes in *Staphylococcus aureus*," Journal of Bacteriology, Mar. 1997, pp. 1614-1621, vol. 179, No. 5, american Society for Microbiology.
Jones, Christopher, "Revised Structures for the Capsular Polysaccharides from *Staphylococcus aureus* Types 5 and 8 Components of Novel glycoconjugate Vaccines," Carbohydrate research, May 2, 2005, pp. 1097-1106, vol. 340, No. 6.
Luong Thanh et al., "Regulation of *Staphylococcus aureus* Capsular Polysaccharide Expression by agr and sarA," Infection and Immunity, Feb. 2002, pp. 444-450, vol. 70, No. 2, american Society for Microbiology.
Link, Andrew J., et al., "Methods for Generating Precise Deletions and Insertions in the Genome of Wild-Type *Escherichia coli*: Application to Open Reading Frame Characterization," Journal of Bacteriology, Oct. 1997, pp. 6228-6237, vol. 179, No. 20, American Society for Microbiology.
Dassy, B., et al., "Production of type 5 capsular polysaccharide by *Staphylococcus aureus* grown in a semi synthetic medium", J. of General Microbiology, (1991), 137, pp. 1155-1162.
Lee J.C., et al., "Effects of in vitro and in vivo growth condtions on expression of Type 8 capsular polysaccharide by *Staphylococcus aureus*", Infection and Immunity, vol. 61, No. 5, May 1993, pp. 1853-1858.
Ouyand, S., "Promoter analysis of the cap8 Operon, involved in type 8 capsular polysaccharide production in *Staphylococcus aureus*", Journal of bacteriology, vol. 1818, No. 8, Apr. 1999, pp. 2492-2500.
Poutrel, B. et al.: "Effects of culture conditions on production of type 5 capsular polysaccharide by human and bovine *Staphylococcus aureus* strains", Clinical and Diagnostic Laboratory Immunology, 1995, 166-171, 2(2).
Taylor, D. et al., "Amiono acid requirements for the growth and production of some exocellular products of *Staphylococcus aureus*", Journal of applied Bacteriology, 1989, 319-329, vol. 66.
Luong, TT et al., "Overproduction of type 8 capsular polysaccharide augments *Staphylococcus aureus* virulence", Infection and Immunity, 2002, 3389-3395, 70(7).
Stringfellow, WT et al., "*Staphylococcus aureus* growth and type 5 capsular polysaccharide production in synthetic media", Applied and Environmental Microbiology, 1991, 618-621, 57(2), Table 1-3.
Robert, "The biochemistry and genetics of capsular polysaccharide production in bacteria", Annual Review of Microbiology, vol. 50:285-315, 1996.
Lee, JC, et al., "Effects of in vitro and in vivo growth conditions on expression of type 8 capsular polysaccharide by *Staphylococcus aureus*", Infect. Immun. May 1993; 61(5):1853-8.
BD Diagnostic Systems Columbia Broth, 2008.

(Continued)

*Primary Examiner* — Maria Leavitt
(74) *Attorney, Agent, or Firm* — McDonnell Boehnen Hulbert & Berghoff LLP

(57) ABSTRACT

The present invention relates to a method for the production of an overproducing *Staphylococcus aureus* strain comprising:

(a) culturing a *Staphylococcus aureus* strain on a culture medium M1, M2 or M3, (b) optionally, recovering the strains thus produced from the culture medium, and also to the use of said strains for the production of polysaccharides.

5 Claims, 1 Drawing Sheet

(56) References Cited

OTHER PUBLICATIONS

BD Diagnostic Systems CTA Medium, Cystine Tryptic Agar, 2008.
Burteau et al., Fortification of a protein-free cell culture medium with plant peptones improves cultivation and productivity of an interferon-gamma-producing CHO cell line In Vitro Cell Dev Biol. Anim. Jul.-Aug. 2003; 39(7):291-6.
Cummings L., Riley L., Black L., Souvorov A., Resenchuk S., Dondoshansky I, Tatusova T. Genomic BLAST: custom-defined virtual databases for complete and unfinished genomes. FEMS Microbiol Lett. Nov. 5, 2002; 216(2): 133-8.
NCBI genomic BLAST with microbial genomes pp. 1-11, 2008.
Mims et al., Medical Microbiology, Third Edition Elsevier Science, 2004, pp. 280-282.
Hurst et al., "Mechanism of the temperature protective effect of salts on *Staphylococcus aureus*", Can J. Microbiol. Apr. 1980;26(4):511-7.

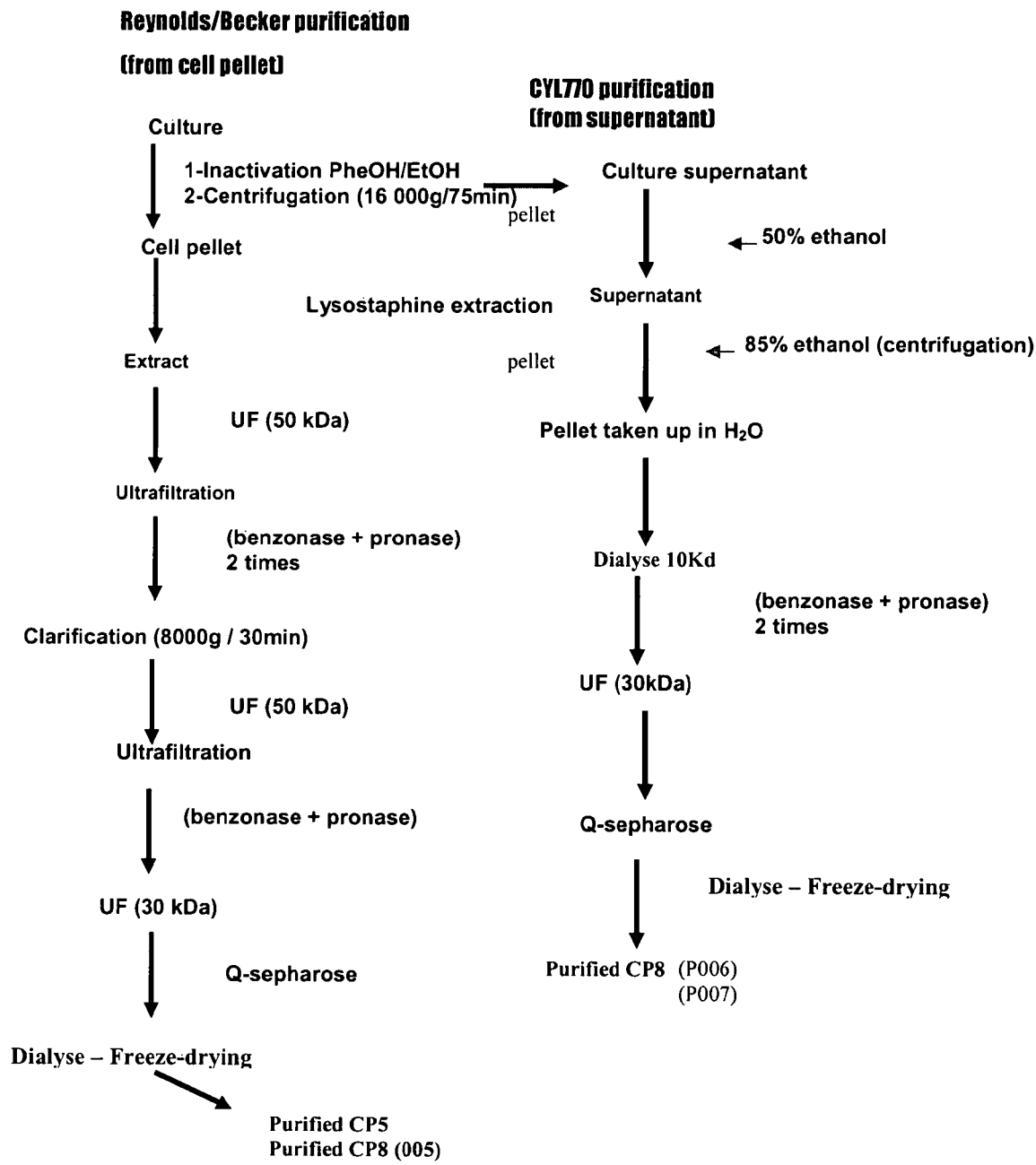

METHOD FOR THE PRODUCTION OF OVERPRODUCING *STAPHYLOCOCCUS AUREUS* STRAINS

CROSS-REFERENCE TO RELATED APPLICATIONS

This application is a divisional application of U.S. patent application Ser. No. 11/408,729, filed Apr. 21, 2006, now U.S. Pat. No. 7,863,013 which is incorporated herein by reference in its entirety and which claims priority to U.S. provisional patent application No. 60/684,103 filed May 24, 2005.

BACKGROUND OF THE INVENTION

The present invention relates to a method for the production of overproducing *Staphylococcus aureus* strains and to their use in a method for the production of capsular polysaccharide.

The *Staphylococcus aureus* capsular polysaccharides, in particular the serotype 5 and 8 polysaccharides, are described in the literature as components of interest for producing a vaccine aimed at protecting against infections due to *Staphylococcus aureus*.

The T5 and T8 strains are microcapsulated and therefore produce small amounts of capsular polysaccharides of interest. The amounts of capsular polysaccharides that have to be included in a vaccine are considerable because of the deficient immune system of the populations targeted (see, for example Fattom, A., et al (1995) *Vaccine* 13, 1288-1293).

In the case of industrial development of such a vaccine, it is therefore important to be able to produce large amounts of T5 and T8 capsular polysaccharides.

SUMMARY OF THE INVENTION

It is with this perspective that the inventors have demonstrated a novel method for substantially increasing the ability of *Staphylococcus aureus* strains to secrete capsular polysaccharide. The inventors therefore provide a method of production that makes it possible to obtain *Staphylococcus aureus* capsular polysaccharide in large amounts.

BRIEF DESCRIPTION OF THE DRAWING

The drawing displays polysaccharide purification protocols for Reynolds/Becker and CYL770 strains.

DETAILED DESCRIPTION OF THE INVENTION

According to a first aspect, the present invention therefore relates to a method for the production of overproducing *Staphylococcus aureus* strains, comprising:
(a) culturing a *Staphylococcus aureus* strain on a culture medium M1 comprising, per liter of culture medium:
  5 to 100 g of plant peptone,
  0.5 to 20 g of yeast extract,
  1 to 30 g of sugar,
  1 to 200 mg of an iron salt selected from the group consisting of $FeCl_3$ and $FeSO_4$,
  1 to 700 mg of a magnesium salt selected from the group consisting of $MgCl_2$ and $MgSO_4$,
  0.1 to 500 mg of $CaCl_2$,
  0 to 50 mg of $ZnCl_2$,
  10 to 250 g of NaCl, preferably 58.5 g/l, and
  the pH of which is within a range of values of from 6.2 to 7.5, and
(b) optionally, recovering the strains from the culture medium.

According to a particular embodiment of the method for the production of overproducing strains, the culture medium M1 of step (a) comprises wheat peptone.

According to an advantageous embodiment of the method for the production of overproducing strains, the culture medium M1 comprises, per liter of culture medium:
  30 g of wheat peptone,
  5 g of yeast extract,
  1 g of D-glucose $H_2O$,
  120 mg of $FeCl_3.6H_2O$,
  400 mg of $MgCl_2.6H_2O$,
  10 mg of $CaCl_2.2H_2O$,
  58.5 g of NaCl,
  5 mg of $ZnCl_2$
  6.8 g of $(NH_4)_2SO_4$,
  6 g of $NH_4Cl$ and pH=6.5.

According to another advantageous embodiment, the medium M1 consists, per liter, of: 30 g of wheat peptone, 5 g of yeast extract, 1 g of D-glucose $H_2O$, 120 mg of $FeCl_3.6H_2O$, 400 mg of $MgCl_2.6H_2O$, 10 mg of $CaCl_2.2H_2O$, 58.5 g of NaCl, 5 mg of $ZnCl_2$, 6.8 g of $(NH_4)_2SO_4$ and 6 g of $NH_4Cl$, pH=6.5.

According to a particular embodiment, the method for the production of overproducing strains comprises a step consisting in preculturing on a preculture medium M0 comprising:
  3 to 50 g of plant peptone,
  0.5 to 20 g of yeast extract,
  1 to 30 g of sugar,
  1 to 200 mg of an iron salt selected from the group consisting of $FeCl_3$ and $FeSO_4$,
  1 to 700 mg of magnesium salt selected from the group consisting of $MgCl_2$ and $MgSO_4$,
  0.1 to 50 mg of $CaCl_2$,
  0 to 50 mg of $ZnCl_2$,
  2 to 50 g of NaCl, preferably 6 g/l, and
  the pH of which is within a range of values of from 6.2 to 7.5.

According to a particular embodiment of the method for the production of overproducing strains, the preculturing step uses a preculture medium M0 comprising, per liter, 3.87 g of wheat peptone.

According to another embodiment of the method for the production of overproducing strains, the preculturing step uses a preculture medium M0 comprising, per liter, 30 g of wheat peptone.

According to an advantageous embodiment of the method for the production of overproducing strains, the preculturing step uses an agar preculture medium M0 comprising: 3.87 g of wheat peptone, 5 g of yeast extract, 1 g of D-glucose $H_2O$, 120 mg of $FeCl_3.6H_2O$, 400 mg of $MgCl_2.6H_2O$, 10 mg of $CaCl_2.2H_2O$, 6 g of NaCl, 5 mg of $ZnCl_2$, 6.8 g of $(NH_4)_2SO_4$, 6 g of $NH_4Cl$, 15 g/l of agar and pH=6.5.

According to another advantageous embodiment of the method for the production of overproducing strains, the preculturing step uses a liquid preculture medium M0 comprising: 30 g of wheat peptone, 5 g of yeast extract, 1 g of D-glucose $H_2O$, 120 mg of $FeCl_3.6H_2O$, 400 mg of $MgCl_2.6H_2O$, 10 mg of $CaCl_2.2H_2O$, 6 g of NaCl, 5 mg of $ZnCl_2$, 6.8 g of $(NH_4)_2SO_4$, 6 g of $NH_4Cl$, and pH=6.5.

According to one embodiment, the method as defined above is a method for the production of overproducing strains of *Staphylococcus aureus* T5.

According to another embodiment, the method as defined above is a method for the production of overproducing strains of *Staphylococcus aureus* T8.

The present invention also relates to an overproducing strain obtained by means of the method as defined above and to the use of said strain for producing capsular polysaccharide. The present invention therefore relates in particular to an overproducing Reynolds strain, an overproducing Becker strain and an overproducing CYL770 strain, obtained by means of the method as described above.

According to another aspect, the present invention therefore provides a method for the production of capsular polysaccharide comprising:

(a) culturing a *Staphylococcus aureus* strain on a culture medium M1 as defined above, (b) inactivating the culture thus produced, and (c) recovering the capsular polysaccharide.

According to one embodiment of the method for the production of capsular polysaccharide, the culturing step uses a culture medium M1 comprising wheat peptone.

According to one embodiment, the method for the production of capsular polysaccharide comprises a preculturing step as defined in relation to the method for the production of overproducing strains.

A subject of the present invention is also a medium M0 suitable for culturing *Staphylococcus aureus*, comprising:
- 3 to 50 g of plant peptone,
- 0.5 to 20 g of yeast extract,
- 1 to 30 g of sugar,
- 1 to 200 mg of an iron salt selected from the group consisting of $FeCl_3$ and $FeSO_4$,
- 1 to 700 mg of a magnesium salt selected from the group consisting of $MgCl_2$ and $MgSO_4$,
- 0.1 to 50 mg of $CaCl_2$,
- 0 to 50 mg of $ZnCl_2$,
- 2 to 50 g of NaCl, preferably 6 g/l, and
- the pH of which is within a range of values of from 6.2 to 7.5, and it preferably relates to an agar or liquid medium M0 comprising, per liter, and advantageously consisting of: 3.87 g or 30 g of wheat peptone and 5 g of yeast extract, 1 g of D-glucose $H_2O$, 120 mg of $FeCl_3.6H_2O$, 400 mg of $MgCl_2.6H_2O$, 10 mg of $CaCl_2.2H_2O$, 6 g of NaCl, 5 mg of $ZnCl_2$, 6.8 g of $(NH_4)_2SO_4$, 6 g of $NH_4Cl$ and pH=6.5.

A subject of the present invention is also a culture medium M1 suitable for the overproduction of *Staphylococcus aureus* capsular polysaccharide, comprising
- 5 to 100 g of plant peptone,
- 0.5 to 20 g of yeast extract,
- 1 to 30 g of sugar,
- 1 to 200 mg of an iron salt selected from the group consisting of $FeCl_3$ and $FeSO_4$,
- 1 to 700 mg of a magnesium salt selected from the group consisting of $MgCl_2$ and $MgSO_4$,
- 0.1 to 500 mg of $CaCl_2$,
- 0 to 50 mg of $ZnCl_2$,
- 10 to 250 g of NaCl, preferably 58.5 g/l, and
- the pH of which is within a range of values of from 6.2 to 7.5, and it preferably relates to a culture medium M1 comprising, per liter, and advantageously consisting of: 30 g of wheat peptone, 5 g of yeast extract, 1 g of D-glucose $H_2O$, 120 mg of $FeCl_3.6H_2O$, 400 mg of $MgCl_2.6H_2O$, 10 mg of $CaCl_2.2H_2O$, 58.5 g of NaCl, 5 mg of $ZnCl_2$, 6.8 g of $(NH_4)_2SO_4$, 6 g of $NH_4Cl$ and pH=6.5.

The inventors have demonstrated that the medium M1 as defined above can be advantageously replaced with a simplified medium M2. The present invention therefore also relates to a method for the production of overproducing *S. aureus* strains and a method for the production of capsular polysaccharides as defined above, in which the medium M1 is replaced with a medium M2 as defined below.

A subject of the present invention is therefore also a culture medium M2, comprising, per liter of culture medium:
- 52.5 to 100 g of plant peptone, advantageously of wheat peptone,
- 0 to 82.5 g of NaCl, advantageously from 5 g to 82.5 g, in particular 41 g/l of NaCl,
- 0 to 15 g/l of a magnesium salt, advantageously from 0.01 to 15 µl, in particular 15 g/l of $MgCl_2.6H_2O$, and
- 0 to 7 g/l of sugar, advantageously from 0.25 to 7 g/l, in particular 0.25 g/l of D-glucose $H_2O$,
- the pH of which is within a range of values of from 6.3 to 6.7, advantageously from 6.4 to 6.6.

According to a particular embodiment, the culture medium M2 comprises, advantageously consists of, 93 g/l of wheat peptone, 41 g/l of NaCl, 0.25 g/l of D-glucose $H_2O$ and 15 g/l of $MgCl_2.6H_2O$, the pH of which is within a range of values of from 6.3 to 6.7.

The inventors have also demonstrated that a culture medium M3, corresponding to a medium M2 in which the plant peptone is replaced with 65 to 85 g/l, advantageously 75 g/l of yeast extract, can be used. The present invention therefore also relates to a method for the production of overproducing *S. aureus* strains and a method for the production of capsular polysaccharides as defined above, in which the medium M1 is replaced with a medium M3 as defined below.

A subject of the present invention is therefore also a culture medium M3, comprising, per liter of culture medium:
- 65 to 85 g of yeast extract, advantageously 75 g/l of yeast extract,
- 0 to 82.5 g of NaCl, advantageously from 5 g to 82.5 g, in particular 41 g/l of NaCl,
- 0 to 15 g/l of a magnesium salt, advantageously from 0.01 to 15 g/l, in particular 15 g/l of MgCl2.6H2O, and
- 0 to 7 g/l of sugar, advantageously from 0.25 to 7 g/l, in particular 0.25 g/l of D-glucose $H_2O$,
- the pH of which is within a range of values of from 6.3 to 6.7.

The present invention will be described in greater detail in the description that follows, with reference to FIG. 1 which provides a representation of the protocol for recovering the polysaccharides.

The inventors have demonstrated, surprisingly, that the culture media M1, M2 and M3 induce a substantial increase in the ability of *Staphylococcus aureus* strains to secrete capsular polysaccharide. Said increase can be demonstrated by measuring the amount of capsular polysaccharide produced, by the ELISA method as described in Example 2.4 below. Said *Staphylococcus aureus* strains exhibiting an increased secretion capacity are, in the context of the present invention, called overproducing strains.

In the context of the present invention, the term "overproducing strains" is therefore intended to mean a *Staphylococcus aureus* strain which, after culturing on a medium M1 or M2 or M3, produces an amount of capsular polysaccharide, in mg/l, as determined by the ELISA method described in Example 2.4, that is at least 3 times, preferably 5 times, and advantageously 10 times, greater than that produced by culturing the same starting strain on Poutrel medium (Poutrel, B et al. (1995). *Clin Diagn Lab Immunol* 2, 166-171 for a description of the medium or Example 1.1 below) under the same culturing conditions.

In the case of a recombinant strain, the term "overproducing strains" is intended to mean a recombinant *Staphylococcus aureus* strain which, after culturing on a culture medium M1 or M2 or M3, produces an amount of capsular polysaccharide, in mg/l, as determined by the ELISA method described in Example 2.4, that is at least twice as much as that produced by culturing the same starting strain on TSB medium (see Example 1.5 for a description of the medium) under the same culturing conditions.

The inventors have demonstrated, surprisingly, that the method for the production of overproducing strains is applicable to the *Staphylococcus aureus* T5 and T8 strains. The inventors have also observed that the method according to the invention is also applicable to recombinant strains which have been genetically modified so as to overproduce their capsular polysaccharide. The inventors have demonstrated this aspect by applying the method according to the invention to the CYL770 strain genetically modified so as to produce T8 capsular polysaccharide in large amounts. After it has been cultured on medium M1 or M2 or M3, the ability of the strain to secrete a T8 capsular polysaccharide increases by a factor of 2, as is described in the examples below.

In the context of the present invention, the term "*Staphylococcus aureus* strains" is therefore intended to mean any *Staphylococcus aureus* strain that expresses a capsule or microcapsule comprising a serotype T5 and/or T8 polysaccharide. By way of nonlimiting examples of suitable strains, mention may be made of the Newman (T5), Reynolds (T5), Lowenstein (T5), Becker (T8), Wright (T8), CYL770 (T8) and CYL1892 (T5) strains.

These strains are available from various institutes or in various collections; mention may in particular be made of the Pasteur Institute Collection (CIP): Reynolds CIP 103313, Becker CIP103314, or the ATCC: Wright ATCC9525, Loweinstein ATCC 49521. In the context of the present invention, the CYL770 (T8) and Reynolds (T5) strains are preferably used. The CYL770 strain is a Becker strain that has been genetically modified so as to produce larger amounts of T8 capsular polysaccharide. This strain can be advantageously used as starting strain in the method for the production of overproducing strains according to the invention and also in the method for the production of polysaccharide according to the invention. A description of the CYL770 strain is given in the article by Luong, T. T and Lee, C. Y (2002), Infect. Immun. 70: 3389-3395. The CYL1892 strain denotes the recombinant *S. aureus* strain obtained from a Reynolds strain (CIP 103313) in which the cap5 operon promoter has been replaced with the strong constitutive promoter of the cap1 operon of the M strain of *S. aureus*, according to the method described by Luong and Lee (2002 *Infect. Immun.* 70: 3389-3395) with the following modifications: the homologous sequences have been replaced with equivalent homologous sequences of the Reynolds strain, the plasmid pCL52.2 has been replaced with the plasmid pCl.10 containing a thermosensitive origin of replication and comprising a cat marker (chloramphenicol acetyltransferase conferring resistance to chloramphenicol). Briefly, a DNA fragment of approximately 1 kb containing the cap5 ORF of the Reynolds strain fused to a fragment of approximately 250 bp containing the Pcap1 promoter is constructed by the overlapping PCR technique. A DNA fragment of approximately 1 kb containing the sequence upstream of the cap5A gene is amplified by PCR from the genome of the Reynolds strain. The two fragments are subsequently cloned into the plasmid pCL10 carrying a temperature-sensitive origin of replication and comprising a cat marker such that the Pcap5 promoter is replaced with the Pcap1 promoter. The plasmid thus constructed is subsequently electroporated into a strain RN4220 and then introduced by transduction using the bacteriophage 52 into the Reynolds strain. The temperature-sensitivity of the origin of replication of the plasmid subsequently makes it possible to promote the homologous recombination by blocking its replication while at the same time applying a selection with chloramphenicol.

In the context of the present invention, the term "capsular polysaccharide" is intended to mean the T5 and/or T8 capsular polysaccharides of the *Staphylococcus aureus* strains, and also the fragments derived therefrom.

In the context of the present invention, the term "culture medium" is intended to mean a medium free of protein of animal origin.

The expression "protein of animal origin" is intended to means proteins obtained from material of animal origin and also any product derived therefrom, such as derivatives originating from the chemical treatment of animal proteins. It is also intended to mean the products of partial or total hydrolysis of these animal proteins, such as peptones, polypeptides, peptides, or the amino acids derived therefrom.

The method for the production of an overproducing strain according to the invention comprises (a) a step consisting in culturing a *Staphylococcus aureus* strain. According to one embodiment, the culturing step uses a culture medium M1 comprising:

5 to 100 g of plant peptone,
  0.5 to 20 g of yeast extract,
  1 to 30 g of sugar,
  1 to 200 mg of an iron salt selected from the group consisting of $FeCl_3$ and $FeSO_4$,
  1 to 700 mg of a magnesium salt selected from the group consisting of $MgCl_2$ and $MgSO_4$,
  0.1 to 50 mg of CaCl2,
  0 to 50 mg of ZnCl2,
  10 to 250 g of NaCl, preferably 58.5 µl, and
  the pH of which is within a range of values of from 6.2 to 7.5.

The protein nitrogen source in the medium M1 used is provided mainly by a plant peptone.

In the context of the present invention, the term "plant peptone" is intended to mean peptones selected from the group consisting of: wheat peptone and pea peptone.

The plant peptones are generally in the form of hydrolysates obtained by enzymatic or chemical treatment of proteins extracted generally from the parts of the plant that contain the highest protein contents, such as the wheatgerm, for example. Plants which have not been chemically modified are preferably used. In the case of chemical treatments, the protein extract is subjected to the action of hydrochloric acid under hot conditions and under pressure. The hydrolysate is then neutralized with sodium hydroxide and the solid by-products are then removed therefrom. In the case of enzymatic treatment, the protein extract is conventionally digested with papain. The peptones obtained consist mainly of a mixture of amino acids, and of small peptides whose MW is ≤1 KD. The peptides whose MW is >1 KD represent less than 30% of the mixture. The commercial preparations referenced under the names Hy-Pea 7404 (from Quest ref 5710565) and Peptone de blé E1 (from Organotechnie ref. 19559) are examples of plant peptone hydrolysates that can be used in the context of the present invention.

The concentration of plant peptone used in the medium M1 is selected by taking into account the protein nitrogen content of the peptone and taking into account the concentration of yeast extract. This content is calculated by the Kjeldahl method. For further details, reference may be made, for example, to the article by Lynch J. M. et al, J. AOAC Int. (1999) 82 (6): 1389-98. Usually, the protein nitrogen contents of the plant peptones selected are between 8% and 15% (weight/weight). In this range of values, the concentration of plant peptone that can be used is from 5 to 100 g per liter of culture medium, preferably from 20 to 50 g/l, and in particular 30 g/l.

The protein nitrogen source in the medium M1 used is also provided by yeast extract. The protein nitrogen contents in the yeast extracts are generally from 9 to 13% (weight/weight). The yeast extract is used at a concentration of 0.5 to 20 g/l of culture medium, and in particular at a concentration of 5 g/l. The protein nitrogen in the culture medium can also be provided in the form of mineral salts; mention may be made, by way of example, of ammonium salts, such as chloride or sulfate. This mineral salts can be used at concentrations which will be adjusted according to the amounts provided by the other nitrogen sources.

The concentrations of protein nitrogen sources are adjusted such that the total protein nitrogen content does not result in a nitrogenous hypercatabolism that may be responsible for the accumulation of toxic waste during the culturing. Furthermore, in order to prevent the appearance of a substantial inhibitory effect due to an excess of vitamins provided by the yeast extract, the latter is only used as a secondary source of protein nitrogen, and preferably at a concentration of 5 g/l.

According to an advantageous embodiment, the culture medium M1 comprises, per liter of medium, 30 g of peptone, preferably of wheat peptone, and 5 g of yeast extract.

The culture medium also comprises a sugar source.

In the context of the present invention, the term "sugar source" is intended to mean any source of sugar of nonanimal origin, that can be metabolized by the bacterium, such as fructose, ribose, xylose, fucose or glucose. Concentrations of the order of 1 to 30 g/liter of culture medium can be used. For glucose, for example, a concentration of 1 g/l is advantageously used.

The culture medium M1 also comprises mineral salts, and in particular iron, magnesium, calcium, zinc and sodium salts, preferably chlorides, in the following amounts:
 from 1 to 200 mg of an iron salt selected from the group consisting of $FeCl_3$ and $FeSO_4$, and in particular 120 mg of $FeCl_3$, per liter of culture medium;
 from 1 to 700 mg of a magnesium salt selected from the group consisting of $MgCl_2$ and $MgSO_4$, and in particular 400 mg of $MgCl_2$, per liter of culture medium;
 from 0.5 to 50 mg of $CaCl_2$, and in particular 10 mg of $CaCl_2$, per liter of culture medium;
 from 0 to 50 mg of $ZnCl_2$, and in particular 5 mg of $ZnCl_2$ per liter of culture medium; and
 from 10 to 250 g of NaCl, preferably 58.5 g, per liter of culture medium.

The mineral salts of Fe, Ca and Mg are conventionally used in hydrated form. In the context of the present invention, the following hydrated salts were used in the culture media: $FeCl_3.6H_2O$, $MgCl_2.6H_2O$, $CaCl_2.2H_2O$.

The medium M1 has an initial pH within a range of values of from 6.2 to 7.5, preferably of 6.5; to do this, any mineral salt conventionally used for its buffering capacity and making it possible to obtain a pH in the value range indicated above can be used if necessary. To determine the pH, it is measured using a pH-meter at ambient temperature.

The medium M1 can also comprise osmotic pressure-regulating agents such as glycerophosphate and/or glycine-betaine, at concentrations of 1 to 10 mM for glycine-betaine and 50 to 100 mM for glycerophosphate, that it may be advantageous to add when the NaCl concentration is greater than 1 M (58 g/l).

The culture medium M1 used preferably corresponds to a liquid medium. It may, however, be in solid form. The solid or agar form is obtained by addition to the liquid medium of a gel-forming substance, usually agar, at a concentration of 10 to 30 g per liter of culture medium.

According to an advantageous embodiment, the culture medium M1 comprises, and preferably consists of, per liter: 30 g of wheat peptone, 5 g of yeast extract, 1 g of D-glucose $H_2O$, 120 mg of $FeCl_3.6H_2O$, 400 mg of $MgCl_2.6H_2O$, 10 mg of $CaCl_2.2H_2O$, 58.5 g of NaCl, 5 mg of $ZnCl_2$, 6.8 g of $(NH_4)_2SO_4$ and 6 g of $NH_4Cl$, and has a pH of 6.5.

The culturing step can be carried out by seeding the medium M1 with an inoculum, for example having an initial OD680 nm of 0.2, and incubating at 37° C. for a period, for example, of approximately 48 to 72 hours in an atmosphere possibly containing $CO_2$ at a concentration of 5 to 10% (for type 5, without $CO_2$, and in the case of the use of the Becker strain, with $CO_2$). The culture volume can vary as required. Volumes of 400 ml to 20 l or larger volumes, for example from 30 l to 100 l, can be used. A ratio of the volume of the culture medium to the volume of the culture container of 20% (V/V) is maintained. For larger volumes, the oxygenation is verified and regulated during the culturing by adjusting the oxygen pressure and appropriate agitation.

The culturing step may comprise, as required, successive cultures in increasing volumes in order to increase the biomass and the amount of polysaccharide produced.

According to an advantageous embodiment, the method for the production of overproducing strains comprises a step consisting in preculturing on a preculture medium M0 comprising, per liter:
 1 to 30 g of plant peptone,
 0.5 to 20 g of yeast extract,
 1 to 30 g of sugar,
 1 to 200 mg of an iron salt selected from the group consisting of $FeCl_3$ and $FeSO_4$,
 1 to 700 mg of a magnesium salt selected from the group consisting of $MgCl_2$ and $MgSO_4$,
 0.1 to 50 mg of $CaCl_2$,
 0.1 to 50 mg of $ZnCl_2$,
 0 to 50 g of NaCl, preferably 6 g/l, and
 the pH of which is within a range of values of from 6.2 to 7.5.

For the definitions of the various constituents, reference may be made to the definitions given above in relation to the culture medium M1.

On the other hand, in the case of the preculturing step, 3.87 g or 30 g of peptone, in particular of wheat peptone, per liter of preculture medium are preferably used. The concentration of NaCl in the medium M0 is preferably 6 g per liter. The preculture medium M0 in the preculturing step is preferably either an agar medium comprising 3.87 g of wheat peptone per liter, or a liquid medium comprising 30 g of wheat peptone per liter.

According to an advantageous embodiment, the preculturing step is carried out by culturing the strain on a preculture medium M0 comprising, and preferably consisting of, per liter: 30 g of wheat peptone, 5 g of yeast extract, 1 g of D-glucose $H_2O$, 120 mg of $FeCl_3.6H_2O$, 400 mg of $MgCl_2.6H_2O$, 10 mg of $CaCl_2.2H_2O$, 6 g of NaCl, 5 mg of $ZnCl_2$, 6.8 g of $(NH_4)_2SO_4$ and 6 g of $NH_4Cl$, pH=6.5.

According to another advantageous embodiment, the preculturing step is carried out by culturing the strain on a liquid or agar preculture medium M0 which comprises, and preferably consists of: 3.87 g of wheat peptone or 30 g/l for the liquid medium M0, 5 g of yeast extract, 1 g of D-glucose $H_2O$, 120 mg of $FeCl_3.6H_2O$, 400 mg of $MgCl_2.6H_2O$, 10 mg of $CaCl_2.2H_2O$, 6 g of NaCl, 5 mg of $ZnCl_2$, 6.8 g of $(NH_4)_2SO_4$ and 6 g of $NH_4Cl$, pH=6.5.

The preculturing step makes it possible to amplify the inoculum. It can be carried out by seeding the preculture medium M0 with a *Staphylococcus aureus* strain, for example in a proportion of $1 \times 10^7$ CFU and incubating at 37° C. for a period that can range, for example, from 5 hours to 20 hours, in an atmosphere possibly containing of from 5 to 10% by volume of $CO_2$ (without $CO_2$ for T5 and in the presence of $CO_2$ when the Becker strain is used). The preculturing step can, in order to increase the biomass, comprise successive precultures in increasing volumes of medium M0. The preculture is then used to seed the liquid medium M1. To do this, an amount of inoculum such that the initial OD680 nm is 0.2 can be used. The culture volume in the preculturing step can vary, conventionally, from 400 ml to 20 l. A ratio of the volume of the preculture medium to the volume of the container of less than or equal to 20% is preferably maintained.

After the culturing step, the strains thus produced can be recovered by centrifugation and conserved in the form of freeze-dried products or of frozen products after the addition of 20% glycerol, or can be used directly in order to seed a larger volume of culture medium, or else can be used directly in the method for the production of capsular polysaccharide according to the present invention.

According to an advantageous embodiment, the production method as defined above corresponds to a method for the production of an overproducing Reynolds strain.

According to another advantageous embodiment, the production method as defined above corresponds to a method for the production of an overproducing CYL770 strain.

The present invention also relates to the overproducing *Staphylococcus aureus* strains, in particular the Reynolds, Becker and CYL770 strains, produced by means of the method as defined above.

The inventors have carried out an experimental plan which shows that the culture medium M1 can be simplified and replaced in the context of the methods according to the present invention with a medium M2 as defined below.

According to another embodiment, step (a) therefore uses a culture medium M2, comprising, per liter of culture medium:
  52.5 to 100 g of plant peptone, advantageously of wheat peptone,
  0 to 82.5 g of NaCl, advantageously from 5 g to 82.5 g, in particular 41 g/l of NaCl,
  0 to 15 g/l of a magnesium salt, advantageously from 0.01 to 15 g/l, in particular 15 g/l of $MgCl_2.6H_2O$, and
  0 to 7 g/l of sugar, advantageously from 0.25 to 7 g/l, in particular 0.25 g/l of D-glucose $H_2O$,
  the pH of which is within a range of values of from 6.3 to 6.7.

For the definition of the terms used, reference will be made to the definitions given above in relation to the culture medium M1.

The results of the experimental plan show that it is not necessary to add sugar to the culture medium M2 when the plant peptone contains a total sugar content of at least 5%. The latter can comprise a mixture of sugars such as: fructose, glucose, mannotriose, raffinose, sucrose or stacchyose. If this is not the case, it is then necessary to add to the culture medium another source of sugar. The sugar can then be added in a proportion of 0.25 g/l to 7 g/l.

According to an advantageous embodiment, the culture medium M2 comprises 0.25 g/l of sugar, in particular of D-glucose $H_2O$.

The culture medium M2 can advantageously contain a magnesium salt selected from the group consisting of $MgCl_2$ and $MgSO_4$. The inventors have demonstrated that the addition of a magnesium salt makes it possible to increase the robustness of the culture medium (the variation ranges of the constituents are substantially narrower in the presence of $MgCl_2$). Magnesium chloride, in particular $MgCl_2.6H_2O$, can therefore be advantageously added to the medium M2 in a range of from 0.01 g/l to 15 g/l of culture medium. The best robustness is observed when the medium M2 contains 15 g/l of $MgCl_2.6H_2O$. Higher concentrations of magnesium salt do not bring about any further increase in robustness.

The inventors have also demonstrated that improved polysaccharide productivity is observed with the medium M2 within a broad range of NaCl concentrations. Specifically, the NaCl can either be absent or can be used within a concentration range of from 5 g/l to 100 g/l, advantageously from 5 g/l to 82.5 g/l of culture medium.

The experimental plan has, moreover, made it possible to show that there is a strong interaction between the concentration of peptone and the concentration of NaCl. It has thus been possible to define concentration ranges that can be advantageously used in the context of the methods according to the present invention.

According to a particularly advantageous embodiment, the medium M2 as defined above comprises 52.5 to 70 g of plant peptone, advantageously of wheat peptone, and 5 to 37 g of NaCl.

According to another particularly advantageous embodiment, the medium M2 as defined above comprises 66 to 82.5 g of plant peptone, advantageously of wheat peptone, and 22 to 74 g of NaCl.

According to another particularly advantageous embodiment, the medium M2 as defined above comprises 60 to 90.5 g of plant peptone, advantageously of wheat peptone, and 35 to 63.5 g of NaCl.

According to another particularly advantageous embodiment, the medium M2 as defined above comprises 79 to 95 g of plant peptone, advantageously of wheat peptone, and 46 to 82.5 g of NaCl.

The media M2 according to these 4 embodiments can advantageously contain 0.25 g/l of glucose, in particular D-glucose, and 15 g/l of $MgCl_2.6H_2O$.

According to a particular embodiment, the culture medium M2 comprises, advantageously consists of, 93 g/l of wheat peptone, 41 g/l of NaCl, 0.25 g/l of D-glucose $H_2O$ and 15 g/l of $MgCl_2.6H_2O$, the pH of which is within a range of values of from 6.3 to 6.7. Such a medium results, for example, in a yield of 40 mg/l of polysaccharide T5 from a Reynolds strain.

The inventors have also shown, by means of an experimental plan, that a medium M2 as defined above, in which the plant peptone is replaced with 65 to 85 g, advantageously 75 g/l of yeast extract, can be used in the methods according to the present invention. This medium is called culture medium M3. The culture medium M3 according to the present invention therefore comprises, per liter of culture medium:
  65 g/l to 80 g/l of yeast extract, advantageously 75 g/l of yeast extract,
  0 to 82.5 g of NaCl, advantageously from 5 g to 82.5 g, in particular 41 g/l of NaCl,
  0 to 15 g/l of a magnesium salt, advantageously from 0.01 to 15 g/l, in particular 15 g/l of $MgCl_2.6H_2O$, and
  0 to 7 g/l of sugar, advantageously from 0.25 to 7 g/l, in particular 0.25 g/l of D-glucose $H_2O$,
  the pH of which is within a range of from 6.3 to 6.7.

Additional experiments have shown that the vegetal peptone concentration range (as defined above) can be extended to 200 g/l of culture media. The M2 and M3 culture media as defined above containing a vegetal peptone in the range of 52.5 to 200 g/l are thus included in the scope of the present invention.

The present invention therefore also relates to the overproducing *Staphylococcus aureus* strains, in particular the Reynolds, Becker, CYL770 and CYL1892 strains produced by means of the method using the culture medium M2 or M3 as defined above.

According to another aspect, the present invention therefore relates to a method for the production of capsular polysaccharide, comprising:
(a) culturing a *Staphylococcus aureus* strain as defined above on a culture medium M1 or M2 or M3 as defined above,
(b) inactivating the culture thus produced, and
(c) recovering the capsular polysaccharide.

The culturing step (a) of the method for the production of capsular polysaccharide can be carried out under the same conditions as those described above in relation to step (a) of the method for the production of overproducing strains, and can also be preceded by a preculturing step as defined above.

The culture resulting from step (a) is then subjected to an inactivation step.

The inactivation step can be carried out by treating the culture with a phenol/ethanol (V/V) mixture in a proportion of 2% by volume, final concentration, and then stirring, for example by means of a magnetic bar, at ambient temperature for 6 hours to 48 hours, depending on the biomass to be treated. The inactivation is verified by means of a mortality test. To do this, 100 microliters of the treated culture are plated out on a Columbia agar 2% NaCl and, in parallel, 100 microliters of the treated culture are seeded in trypcase soy broth supplemented with $1/30^{th}$ of horse serum. The cultures are incubated for 48 h at 37° C. in the static position, the stoppers of the broth flasks remaining unscrewed. The inactivation of the cultures can be controlled by a method comprising an amplification step in TSB medium (without the addition of serum) with shaking at 37° C. for 16 to 18 h, and then a petri dish of Columbia agar 2% NaCl is inoculated with 150 μl of culture thus amplified. The dish is itself placed at 37° C. for 16 to 18 h and then observed. A lack of colonies attests to the successful inactivation of the treated culture. A lack of viable bacteria is reflected by a lack of growth after incubation for 24 hours at 37° C. Once the mortality of the culture has been established, the capsular polysaccharide is recovered. The recovery step comprises extracting the polysaccharide from the cells. Various extraction techniques have been described in the literature and can be used in the context of the present invention. Reference may, for example, be made to the articles by Lee J. C. Infect. Immunu. 1993; 67:1853-1858; Dassy B. et al J. Gen. Microbiol. 1991; 137: 1155-1162. A method of extraction by autoclaving at 121° C. is illustrated in Example 2.3. An extraction technique using lysostaphin is described in Example 2.5.

In the case of the CYL 770 strain, most of the polysaccharide is secreted into the culture supernatant and can therefore be recovered directly from the latter. To do this, at the end of the culture, the medium is centrifuged and the cell pellet is removed.

The resulting capsular polysaccharide can then, if necessary, be purified. Various purification techniques have been described in the literature and can be used in the context of the present invention. Reference may, for example, be made to the articles by Lee J. C. et al 1987; 55: 2191-2197; Fattom A. et al Infect. Immun. 1990; 58: 2367-2374. A purification technique is illustrated in Example 2.5.

Analysis of the molar composition of monosaccharide and proton NMR analysis at 500 MHz show that a polysaccharide is obtained, the structure of which is in accordance with that described in the literature, with a degree of 0-acetylation of greater than 70% and a degree of purity of at least 70%. The residual materials are present in the final product in a proportion of approximately 0.5 to 3% (w/w) of residual materials of protein type and less than 0.1% (w/w) of residual nucleic acids and less than of 5% (w/w) of residual lipotechoic acid and residual techoic acid.

The amount of capsular polysaccharide obtained can be evaluated by the ELISA technique as described in Example 2.4.

The method for the production of PS according to the invention can therefore advantageously be used for producing T5 polysaccharide, preferably from a Reynold strain such as CIP 103313, and T8 polysaccharide, preferably from the CYL770 strain.

According to another aspect, the present invention therefore relates to a medium M0 as defined above, suitable for culturing *Staphylococcus aureus*.

In the context of the present invention, the expression "medium suitable for culturing *Staphylococcus aureus*" is intended to mean a medium that makes it possible to obtain, firstly, an increase in the biomass by a factor of at least 10 as determined by measuring the optical density at 680 nm and, secondly, a viability such that the OD/CFU ratio is at least 1 OD unit=$10^8$ CFU/ml. To determine this OD/CFU ratio, the bacterial suspension, the optical density of which has been measured using a spectrophotometer, is diluted in PBS buffer using 10-fold dilutions. The number of CFU contained in these dilutions is evaluated after seeding of the latter on a petri dish containing a nutritive medium (such as Colombia agar). After incubation for 24 hours at 37° C., the viable bacteria are counted and the correspondence between the number of viable bacteria, expressed as colony forming units (CFU), and the optical density (OD) can thus be established.

According to another aspect, the present invention also relates to the culture media M1, M2 and M3 as defined above, suitable for the overproduction of *Staphylococcus aureus* capsular polysaccharide.

In the context of the present invention, the expression "medium suitable for the overproduction of capcular polysaccharide" is intended to mean a medium that produces an increase in the ability of a *Staphylococcus aureus* strain to secrete capsular polysaccharide, which results in a production of capsular polysaccharide, as determined by an ELISA assay as defined in Example 2.4, that is at least 3 times, preferably at least 5 times, and in particular at least 10 times, greater than that produced by culturing the same starting strain under the same culturing conditions, but on the Poutrel medium.

In the case of recombinant strains, it is considered that the medium is suitable for the overproduction of capsular polysaccharide if it produces an increase in the ability of a recombinant *Staphylococcus aureus* strain to secrete capsular polysaccharide, resulting in a production of capsular polysaccharide, as determined by an ELISA assay as defined in Example 2.4, that is at least twice as much as that produced by culturing the same starting strain under the same culturing conditions, but on a TSB medium.

The present invention will now be described in greater detail in the following examples, which are given purely by way of illustration of the invention and can in no way be considered as limiting the scope of the latter.

Example No. 1

Preparation of Culture Media

Firstly, stock solutions of each of the constituents are prepared. To do this, the constituents are weighed out on a precision balance and dissolved in ultrafiltered water (unless otherwise indicated). The solutions thus obtained are then filtered through a 0.22 micron stericup and stored at +4° C. in the dark. The stock solutions of wheat peptones, of yeast extract and of $FeCl_3$ are prepared extemporaneously.

1.1—Poutrel Medium

The Poutrel medium is prepared as indicated in the article by Poutrel et al., (Poutrel, B et al. (1995). *Clin Diagn Lab Immunol* 2, 166-171) by mixing the various stock solutions. The pH is then adjusted to 7 by adding 30% NaOH and the medium is then filtered through 0.22 micron.

The final composition, in g/l, of the medium is: L-cystine: 0.24 g/l; L-aspartic acid: 2.4 g/l; L-glutamic acid: 2.4 g/l; L-proline: 2.4 g/l; L-arginine: 0.36 g/l; L-glycine: 2.4 g/l; L-histidine: 0.48 g/l; L-lysine HCl: 0.6 g/l; L-serine: 2.4 g/l; L-valine: 0.48 g/l; L-tyrosine: 0.18 g/l; L-threonine: 2.4 g/l; L-alanine: 2.4 g/l; L-isoleucine: 0.6 g/l; L-leucine: 0.6 g/l; L-phenylalanine: 0.2 g/l; L-tryptophan: 0.06 g/l; L-methionine: 0.18 g/l; D-glucose: 10 g/l; nicotinic acid: 11.94 mg/l; thiamine HCl: 0.6 mg/l; ammonium sulfate: 6.84 g/l; potassium dihydrogen phosphate: 1.34 g/l; sodium diphosphate: 14.38 g/l; calcium chloride: 5 mg/l; cobalt chloride hexahydrate: 2.4 mg/l; copper sulfate: 0.5 mg/l; manganese sulfate: 5.6 mg/l; sodium chloride: 5.8 mg/l; zinc chloride: 3.4 mg/l; iron chloride: 27 mg/l; magnesium sulfate: 247 mg/l.

1.2—Agar Medium M0, Liquid Medium M0, M1 Medium

For the agar medium M0:

Firstly, 150 ml of agar base are prepared by dissolving 3 g of agar in 150 ml of ultrafiltered $H_2O$. The resulting composition is placed in a boiling water bath until the grains of agar disappear (approximately 30 min) and then sterilized in an autoclave for 30 min at 116° C.

The agar medium M0 is then prepared by mixing the various stock solutions (in the order indicated in the composition below), filtering the resulting mixture through a 0.22 micron stericup and adding the mixture thus obtained in 50 ml to the agar base so as to obtain a medium containing, in g per liter:

wheat peptone: 3.87 g; yeast extract: 5 g; D-glucose $H_2O$: 1 g; NaCl: 6 g; $MgCl_2.6H_2O$: 0.4 g; $(NH_4)_2SO_4$: 6.8 g; $NH_4Cl$: 6 g; $FeCl_3.6H_2O$: $120\times10^{-3}$ g; $ZnCl_2$: $5\times10^{-3}$ g; $CaCl_2.2H_2O$: $10\times10^{-3}$ g.

8 petri dishes are then poured.

The wheat peptone which was used corresponds to the wheat peptone from Organotechnie (ref. 19559). The yeast extract used corresponds to the extract from Beckton Dickinson (ref. 212750):

For the Liquid Medium M0:

The liquid medium M0 is prepared by mixing the various stock solutions in the order indicated in the composition below and filtering the resulting mixture through a 0.22 micron stericup so as to obtain a medium containing, in g per liter:

wheat peptone: 30 g; yeast extract: 5 g; D-glucose $H_2O$: 1 g; NaCl: 6 g; $MgCl_2.6H_2O$: 0.4 g; $(NH_4)_2SO_4$: 6.8 g; $NH_4Cl$: 6 g; $FeCl_3.6H_2O$: $120\times10^{-3}$ g; $ZnCl_2$: $5\times10^{-3}$ g; $CaCl_2.2H_2O$: $10\times10^{-3}$ g; pH=6.5.

For the Medium M1

The medium M1 is prepared by mixing the various stock solutions in the order indicated in the composition below and filtering the resulting mixture through a 0.22 micron stericup so as to obtain a medium containing, in g per liter:

wheat peptone: 30 g; yeast extract: 5 g; D-glucose $H_2O$: 1 g; NaCl: 58.5 g; $MgCl_2$: 0.4 g; $(NH_4)_2SO_4$: 6.8 g; $NH_4Cl$: 6 g; $FeCl_3$: $120\times10^{-3}$ g; $ZnCl_2$: $5\times10^{-3}$ g; $CaCl_2$: $10\times10^{-3}$ g

1.3—Colombia Agar 2% NaCl

For 1 liter of medium, 44 g of Columbia "Blood Agar Base" (Difco ref. 279240) are weighed out, and then 500 ml of sterile ultrafiltered $H_2O$ are added. The mixture obtained is incubated in a waterbath at 100° C. for approximately 30 minutes (until complete dissolution and a clear solution had been obtained). 500 ml of sterile ultrafiltered $H_2O$ are then added. The solution is dispensed into 200 ml Schott flasks, and then sterilized by autoclaving at 116° C. for 30 minutes.

The media are then kept at 55° C. (waterbath) before being poured into petri dishes (25 ml/dish). Before pouring the dishes, 13.3 ml of 30% NaCl (filtered through 0.22 μm) are added per 200 ml flask, so as to obtain a final concentration of 2% (=2 g/100 ml).

1.4-Tryptic Soy Agar (GTS)

For 1 liter of medium, 40 g of "Tryptic Soy Agar" (Difco ref. 236950) are weighed out, and 500 ml of sterile ultrafilted $H_2O$ are then added. The mixture obtained is incubated in a waterbath at 100° C. for approximately 30 minutes (until complete dissolution and a clear solution are obtained). 500 ml of sterile ultrafiltered $H_2O$ are then added. The solution is dispensed into 200 ml Schott flasks, and then sterilized by autoclaving at 116° C. for 30 minutes. The media are then kept at 55° C. (waterbath) before being poured into petri dishes (25 ml/dish).

1.5—"Bacto Tryptic Soy" Broth (TSB)

For 1 liter of medium, 30 g of "Bacto Tryptic Soy" (Difco Ref. 211825) are weighed out, and 500 ml of sterile ultrafiltered $H_2O$ are then added. The mixture obtained is incubated in a waterbath at 100° C. for approximately 30 minutes (until complete dissolution and a clear solution are obtained). 500 ml of sterile ultrafiltered $H_2O$ are then added. The solution is dispensed into 200 ml Schott flasks, and then sterilized by autoclaving at 116° C. for 30 minutes. The media are then kept at 55° C. (waterbath) before being poured into petri dishes (25 ml/dish).

Example 2

Evaluation of the Production of Type 5 Capsular Polysaccharide (CP5) Under Various Culture Conditions

2.1—Culturing the Reynolds Strain

Frozen materials were prepared in two different ways, depending on whether it is desired to operate under conditions without compounds of animal origin or under standard conditions. For the standard conditions, a starting freeze-dried material is taken up on a Colombia agar +2% NaCl. The latter is cultured for 18 hours at 37° C. with or without $CO_2$ depending on the strain. The culture is again subcultured on a new agar dish for 4 hours at 37° C. in order to obtain microorganisms in the exponential growth phase. The culture is then recovered in a tryptic soy broth to which 20% of glycerol is added. When conditions free of compounds of animal origin are required, the preculturing is carried out on medium M0 for 18 hours at 37° C. and the inoculum is then used to subculture a liquid medium M0. The freezing is also carried out after the addition of 20% glycerol.

100 μl of frozen Reynolds material obtained by the first method mentioned above are taken up in 900 μl of PBS.

Two petri dishes of agar medium M0 and two petri dishes of columbia agar 2% NaCl are seeded with a layer of 150 µl of bacterial suspension per dish, and incubated for 18-20 h at 37° C.

The layers are scraped up and resuspended in 5 ml of PBS. The $OD_{680nm}$ of the suspensions is measured, and makes it possible to determine the volume of preculture necessary in order to seed 50 ml Erlenmeyer flasks at $OD_{680nm}$=0.2.

The preculture on Columbia agar 2% NaCl is used to seed an Erlenmeyer containing Poutrel medium, and the preculture on agar M0 (18-20 h at 37° C.) is used to seed an Erlenmeyer flask containing liquid medium M0 and an Erlenmeyer flask containing medium M1. The volumes can vary according to the assays, and are most commonly 50 ml. In order to maintain correct oxygenation, the volume of medium is less than or equal to 20% of the volume of the Erlenmeyer flask.

After verification of the initial $OD_{680nm}$ values, the Erlenmeyer flasks are shaken (×100 rpm) at 37° C.

The cultures are monitored by measuring the OD at 680 nm at $t_0$, $t_{8h}$, $t_{24h}$, $t_{32h}$, $t_{48h}$, $t_{56h}$, and $t_{72h}$, and the pH is measured initially and at 72 h of culture. The results obtained on the 50 ml cultures are reported in Tables 1 and 2 below.

TABLE 1

| Strain | Preculture medium | OD/CFU for OD680 = 1 | Standard deviation |
|---|---|---|---|
| Reynolds | Columbia agar 2% NaCl | 5.3E+08 | 8.2E+07 |
| Reynolds | Agar M0 | 4.2E+08 | 1.7E+08 |

TABLE 2

| | OD 68 nm measurement | | |
|---|---|---|---|
| Time in hours | Poutrel | Agar M0 | M1 |
| 0 | 0.2 | 0.2 | 0.2 |
| 8 | 2.8 | 2.6 | 2.7 |
| 24 | 6.7 | 6.2 | 4.0 |
| 32 | 9.1 | 8.0 | 4.7 |
| 48 | 10.1 | 8.4 | 6.1 |
| 56 | 8.6 | 8.7 | 6.4 |
| 72 | 8.1 | 8.6 | 5.7 |
| initial pH | 7 | 6.5 | 6.5 |
| final pH | 8.5 | 8.5 | 8.5 |

2.2—Inactivation of the Culture

At 72 h, the cultures are dispensed into four 1 l Schott flasks each containing 750 ml of culture. 15 ml of phenol/ethanol (v/v) for 750 ml of culture, i.e. a final concentration of 2%, are added and the mixture is stirred using a magnetic bar at ambient temperature for approximately 48 h.

The mortality test is carried out in the following way:

100 µl al of treated culture are plated out on Columbia 2% NaCl, and

100 µl of treated culture are seeded in tryptic soy broth+ 1/30th horse serum, and then incubated for 48 h at 37° C. (the stoppers of the flaks of triptic soy broth are left unscrewed). The cultures thus inactivated are used to extract the polysaccharide and to evaluate the amount produced by ELISA.

2.3—Extraction of the Polysaccharide Produced

The inactivated 72 h cultures are then centrifuged for 30 min at 3500 rpm at +4° C., and the culture supernatants are separation and stored at +4° C. The pellets are taken up in 5 ml of PBS and autoclaved for 60 min at 121° C., and then centrifuged for 30 min at 25 000 g and +4° C. the supernatant (extract 1) is recovered. The pellets are taken up in 5 ml of PBS, autoclaved for 60 min at 121° C. and centrifuged for 30 min at 25 000 g and +4° C. The supernatant (extract 2) is recovered. Extracts 1 and 2 are combined and treated with 50 micrograms/ml of proteinase K for 1 h at 37° C., and the protein is then inactivated for 20 minutes at 75° C.

2.4—Evaluation of the Amount of Polysaccharide Produced, by ELISA

The polyclonal sera directed against the type 5 or type 8 capsule were produced according to the method described by Karakawa et al., J Clin Microbiol. 1985 September; 22(3): 445-7. The monoclonals used were produced by the protocol as described by Hochkeppel et al., J Clin Microbiol. 1987 March; 25(3):526-30, and were given to us by the Pasteur Institute.

The amount of capsular polysaccharide produced is determined by ELISA. To do this, a sandwich ELISA assay is carried out on 96-well plates (Nunc, Roskilde, Denmark). In a first step, an anti-CP5 monoclonal antibody (1 microgram per ml in 0.05 M sodium carbonate buffer, pH=9.6 (Sigma)– 100 ng/well) is deposited in the wells, and the plates are incubated overnight at 4° C. The plates are then washed 4 times with 300 microliters per well of PBS buffer (Eurobio) supplemented with 0.05% of tween 20 (Sigma) (PBS-Tween) and then saturated for one hour at 37° C. with 250 microliters per well of PBS-Tween supplemented with 1% (vol/weight) of BSA (Eurobio) (PBS-Tween-BSA). The plates are then washed three times with the PBS-Tween solution.

Serial 2-fold dilutions of the extracts from step 2.3 are prepared using the PBS-Tween-BSA solution, and added in a proportion of 100 microliters per well. The plates are incubated for 90 minutes at 37° C. and then washed 4 times with PBS-Tween. Anti-CP5 rabbit polyclonal antibodies produced according to the protocol of Karakawa (Karakawa et al., 1985, J. Clin. Microbiol. 1985, September; 22(3): 445-7) are diluted in PBS-Tween-BSA (1/2000) and then added to the wells in a proportion of 100 microliters per well, and the plates are incubated for 90 minutes at 37° C. The plates are then washed 4 times with PBS-Tween. The anti-rabbit goat IgG peroxidase conjugate (Southern biotech.), diluted in PBS-Tween-BSA (1/6000), is added in a proportion of 100 microliters per well and the plate is incubated for 1 hour at 37° C. The plates are washed 8 times with 300 microliters of PBS-Tween per well and 100 microliters per well of a solution of TMB substrate (TEBU) are added, followed by incubation in the dark for 15 min at ambient temperature (approximately 22° C.). The enzyme reaction is stopped by adding 100 microliters of 1M $H_3PO_4$ 1M (Sigma) per well.

An automatic plate reader (Versamax) then measures the optical density at 450 nm. The value of the control is subtracted and the amount is evaluated by comparison with a standard curve.

The results are reported in Table 3 below.

| Culture medium | Preculture | Culture vol. (ml) | Initial OD 680 | Final OD 680 | CP5 ELISA assay (X3) | |
|---|---|---|---|---|---|---|
| | | | | | Mean (microg/ml of culture) | Standard deviation |
| Poutrel | Columbia agar 2% NaCl | 50 | 0.2 | 8.1 | 3.6 | 0.3 |
| Liquid M0 | Agar M0 | 50 | 0.2 | 8.6 | 9.7 | 1.2 |
| M1 | Agar M0 | 50 | 0.2 | 5.7 | 36.0 | 1.5 |

2.5—Extraction and Purification of Polysaccharide CP5

The Reynolds strain is cultured as is described in point 2.1 according to a protocol comprising a preculture on agar medium M0 and then a culture in 400 ml of medium M1 in Erlenmeyer flasks. The cultures are combined so as to obtain 3 liters of culture from which the T5 polysaccharide produced is extracted and purified.

The entire culture is inactivated by treatment with phenol-ethanol (final concentration 2% V/V) and then centrifuged 30 nm to 25 000 g. A pellet of approximately 10.9 g of wet inactivated microorganisms per liter of culture is obtained.

The microorganisms are suspended in a proportion of 0.5 g/ml of 50 mM Tris, 2 mM $MgSO_4$, pH 7.5. An aqueous solution of lysostaphin at 5 mg/ml is added so as to obtain a final concentration of 100 µg/ml. After incubation for 4 hours at 37° C. with magnetic stirring, a solution of benzonase at a final concentration of 5 U/ml is added and the incubation is carried out for 2 hours at 37° C. with magnetic stirring.

After centrifugation (25 000 g, 30 min), the extraction supernatants are harvested, combined and ultrafiltered. The supernatant is diluted beforehand to ¼ in $H_2O$ so as to obtain a sufficient volume for the ultrafiltration system. The ultrafiltration is carried out on 2 UF 59 kD cassettes under the following conditions:$H_2O$: 10 volumes; then 50 mM Tris, pH 8.0: 3 volumes. The volume of retentate remains constant during the ultrafiltration. The retentate constitutes what is called the CP5 extract.

The CP5 extract is incubated at 37° C. in the presence of $MgCl_2$ (final concentration of 1 mM) and benzonase (final concentration of 5 U/ml, i.e. ~40 Upper gram of wet microorganisms treated) with stirring. After incubation for 3 hours, the benzonase is added at a final concentration of 5 U/ml, and the incubation is continued for 3 hours. An aqueous solution of pronase at 10 mg/ml is added so as to obtain a final concentration of 4 U/ml (i.e. ~30 Upper gram of wet microorganisms treated), supplemented with $CaCl_2$ at a final concentration of 1 mM. The mixture is then incubated for 15 hours at 37° C. A 50 kD ultrafiltration is carried out, in order to remove the nucleic acid and protein fragments, on two UF 50 Kd cassettes, under the following conditions: $H_2O$: 10 volumes, then 50 mM Tris, pH 8.0: 3 volumes. The volume of retentate remains constant during the ultrafiltration. The following are added to the retentate obtained above: $MgCl_2$ at a final concentration of 1 mM, benzonase at a final concentration of 0.1 U/ml, and the mixture is incubated for 3 hours with magnetic stirring.

An aqueous solution of pronase at 10 mg/ml is added at a final concentration of 0.1 U/ml, supplemented with $CaCl_2$ at a final concentration of 1 mM, and the mixture is then incubated for 2 hours at 37° C.

An ultrafiltration on two UF 30 KD cassettes is then carried out under the following conditions: $H_2O$: 10 volumes, then 50 mM Tris, pH 7.5: 3 volumes. The retentate obtained exhibits a whitish precipitate/cloud, which is removed by centrifugation at 8000 g for 30 min.

A purification step on ion exchange chromatography is then carried out.

It makes it possible to remove the residual materials, in particular the teichoic acid (TA) and the lipoteichoic acid (LTA).

The following conditions are used: three 5 ml Hi Trap Q HP columns are connected in series (Ref: Amersham 17-1154-01); equilibration buffer: 20 mM Tris, pH 7.5; flow rate: 2 ml/min; sample injected in equilibration buffer.
Elution:
  20 mM Tris, pH 7.5: 5 column volumes
  gradient of 20 mM Tris, pH 7.5, 0-0.5 M NaCl: 10 column volumes
  mM Tris, 0.5 M NaCl, pH 7.5: 5 column volumes
  gradient of 20 mM Tris, pH 7.5, 0.5-1M NaCl: 5 column volumes
  20 mM Tris, 1M NaCl, pH 7.5: 5 column volumes
  20 mM Tris, pH 7.5: 5 column volumes The elution is monitored by measurement of the absorbance at 206 and 280 nm. A CZE analysis makes it possible to identify the various constituents eluted during the chromatography.

The CP5 polysaccharide is eluted at a concentration of NaCl of between 0.2 M and 0.3 M. Under the chromatographic conditions used, said polysaccharide is clearly separated from the residual materials, in particular the teichoic acid, which is eluted between 0.36 M and 0.48 M of NaCl, and the lipoteichoic acid, which is eluted between 0.74 M and 0.86 M of NaCl.

The fractions containing the CP5 are combined and dialyzed at +4° C. against 20 volumes of a 0.5 M aqueous NaCl solution (2-3 baths), and then against 20 volumes (3-4 baths) of ultrafiltered water. The Tris is thus eliminated.

The purified product is freeze-dried and conserved at −20° C.

From 3 liters of culture, 74 mg of T5 capsular polysaccharide are obtained at the end of purification. The characteristics of the product are reported in Table 4 below.

TABLE 4

| CP5 assay | O-acetyl (CP by weight of powder) | | O-acetyl (CP CE assay) | | proteins | DNA |
|---|---|---|---|---|---|---|
| Analytical method | | | | | | |
| NMR | colorimetry | | | | Micro BCA direct | Picogreen |
| Units | | | | | | |
| % relative to the weight of powder | Mmol/mg CP | Mol/mol UR | Mmol/mg CP | Mol/mol UR | % W/W relative to the weight of powder | % W/W relative to the weight of powder |
| Results: 80% | 1.32 | 0.87 | 1.65 | 1.08 | 2.7% | <0.1% |

Example 3

Evaluation of the Type 8 Capsular Polysaccharide (CP8) Productivity Under Various Culturing Conditions The evaluation is carried out on the Becker and CYL770 strains.

3.1—Culturing the Becker Strain

The frozen materials are prepared in two different ways depending on whether it is desired to operate under conditions without compounds of animal origin or under standard conditions. For the standard conditions, an initial freeze-dried material is taken up on a Colombia agar +2% NaCl. The latter is cultured for 18 hours at 37° C. with or without $CO_2$ depending on the strain. The culture is again subcultured on a new agar dish for 4 hours at 37° C. in order to obtain microorganisms in the exponential growth phase. The culture is then recovered in tryptic soy broth, to which 20% of glycerol is added. When conditions free from compounds of animal origin are required, the preculturing is carried out on medium M0 for 18 hours at 37° C. and the inoculum is then used to subculture a liquid medium M0. The freezing is also carried out after the addition of 20% glycerol.

100 µl of Becker frozen material prepared according to the tryptic soy broth method is taken up in 900 µl of PBS. Three petri dishes of agar M0, two petri dishes of columbia agar 2% NaCl, and one GTS petri dish are seeded with a layer of 150 µL of bacterial suspension per dish. The dishes are incubated for 18/20 h at 37° C.+5% $CO_2$.

The layers are scraped up and resuspended in 5 ml of PBS. The $OD_{680nm}$ of the suspensions is measured, and makes it possible to determine the volume of preculture required to seed 50 ml Erlenmeyer flasks at $OD_{680nm}$=0.2.

The preculture on columbia agar 2% NaCl is used to seed an Erlenmeyer flask containing Poutrel medium, the preculture on GTS is used to seed an Erlenmeyer flask containing TSB, and the preculture on agar medium M0 is used to seed an Erlenmeyer flask containing liquid medium M0 and an Erlenmeyer flask containing medium M1.

In order to maintain correct oxygenation, the volume of medium is less than or equal to 20% of the volume of the Erlenmeyer flask.

After verification of the initial $OD_{680nm}$ values, the Erlenymer flasks are shaken at 100 rpm at 37° C.

Similar experiments are carried out in Erlenmeyer flasks containing 400 ml of culture medium.

3.2—Culturing the CYL770 Strain

For the recombinant CYL770 strain, the method for preparing the frozen materials uses subculturing of the initial frozen material on TSB medium or on a liquid medium M0. The culturing is carried out for 5 hours at 37° C. with shaking. The freezing is carried out after the addition of 20% of glycerol to the medium.

One frozen CYL770 material of 1 ml thus obtained is taken up with 10 ml of liquid medium M0 and then placed in a 50 ml Erlenmeyer flask and incubated for 18/20 h at 37° C. with shaking at 100 rpm. A second frozen CYL770 material is taken up in 10 ml of TSB medium and then placed, with shaking, under the same conditions as before.

The $OD_{680nm}$ of the liquid precultures is measured, and makes it possible to determine the volume of preculture required to seed the 50 ml Erlenmeyer flasks at $OD_{680nm}$ 0.2.

The preculture in TSB makes it possible to seed an Erlenmeyer flask containing TSB, and the preculture in liquid M0 makes it possible to seed an Erlenmeyer flask containing medium M1. In order to maintain correct oxygenation, the volume of medium is less than or equal to 20% of the volume of the Erlenmeyer flask.

After verification of the initial $OD_{680nm}$ values, the Erlemeyer flasks are shaken at 100 rpm at 37° C.

Similar experiments are carried out in Erlenmeyer flasks containing 400 ml of culture medium.

3.3—Monitoring of Cultures

The cultures are monitored by measuring the OD at 680 nm at $t_0$, $t_{8h}$, $t_{24h}$, $t_{32h}$, $t_{48h}$, $t_{56h}$, and $t_{72h}$. The pH is measured initially and at 72 h of culture. The results of the 50 ml cultures are reported in Table 5 below.

| Time in | Becker | | | | CYL770 | |
| --- | --- | --- | --- | --- | --- | --- |
| hours | Poutrel | Liquid M0 | M1 | TSB | TSB | M1 |
| 0 | 0.3 | 0.3 | 0.3 | 0.2 | 0.2 | 0.2 |
| 8 | 3.3 | 3.2 | 3.6 | 5.7 | 3.3 | 2.3 |
| 24 | 7.4 | 8.0 | 4.9 | 7.1 | 5.6 | 3.4 |
| 32 | 7.8 | 8.6 | 5.9 | 7.4 | 5.9 | 4.0 |
| 48 | 8.3 | 8.6 | 6.3 | 7.5 | 4.7 | 5.8 |
| 56 | 8.1 | 8.5 | 5.3 | 5.7 | 3.9 | 5.1 |
| 72 | 7.0 | 7.5 | 6.6 | 5.8 | 2.9 | 5.4 |
| initial pH | 7 | 6.5 | 6.5 | 7 | 7 | 6.5 |
| final pH | 9 | 8.5 | 8.5 | 9 | 9 | 8.5 |

3.4—Inactivation of Cultures

The cultures are inactivated according to the same protocol as that described in point 2.2 above. The extraction of the polysaccharide produced is carried out according to the same protocol as that described in point 2.3 above.

3.5—Evaluation of the Amount of Polysaccharide Produced, by ELISA

The evaluation of the amount of polysaccharide produced is carried out using the same ELISA assay as that described in point 2.4 above, except that the antibodies used are anti-CP8 antibodies and the assay is carried out on the pellet extracts and on the culture supernatant. The adsorption was carried out with an ascites containing the monoclonal K8-24 diluted to 1/20 oooth and the rabbit polyclonal antibody is an adsorbed serum diluted to 1/1000th.

The results obtained for cultures of 50 ml and of 400 ml are reported in Table 6 below. For the 400 ml cultures, the analysis is carried out each time on a single sample of 50 ml of a culture and the total amount is then calculated and reported in Table 6.

TABLE 6

| | | | ELISA assay of CP8 (X2) | | | |
| --- | --- | --- | --- | --- | --- | --- |
| | | | pellet | | supernatant | |
| Strain | Culture | Preculture | Mean (microgram/ ml of culture) | Standard deviation | Mean (microgram/ ml of culture) | Standard deviation |
| Becker (50 ml) | Poutrel | Columbia agar 2% NaCl | 1.3 | 0 | 1.8 | 0 |
| | liquid M0 | agar M0 | 1.9 | na | 3.6 | na |
| | M1 | agar MO | 14.0 | 1.6 | 43.2 | 2.2 |
| | TBS | GTS | 0 | 0 | 0 | 0 |

TABLE 6-continued

| | | | ELISA assay of CP8 (X2) | | | |
| | | | pellet | | supernatant | |
| Strain | Culture | Preculture | Mean (microgram/ ml of culture) | Standard deviation | Mean (microgram/ ml of culture) | Standard deviation |
| --- | --- | --- | --- | --- | --- | --- |
| Becker (400 ml) | M1 | agar M0 | 23.04 | | 57.6 | |
| CYL770 (50 ml) | M1 | liquid M0 | 8.7 | 0.5 | 534.2 | 75.2 |
| | TSB | TSB | 4.7 | 1.3 | 244 | na |
| CYL770 (400 ml) | M1 | liquid M0 | 27.18 | na | 579.6 | na |
| | TSB | TSB | 3.6 | na | 216 | na | na: not applicable 3.6—Recovery and Purification of the PS Produced

The T8 polysaccharide was recovered from the 400 ml Erlenmeyer flask cultures of the Becker strain in medium M1 using the method as described in Example 2 for obtaining the T5 polysaccharide.

The T8 polysaccharide was also purified from the 400 ml Erlenmeyer flask cultures of the CYL770 strain in medium M-1 and from the cultures on TSB medium. To do this, 800 ml of culture are inactivated by treatment with phenol-ethanol according to the method described above, and then centrifuged for 30 min at 25 000 g. 720 ml of supernatant were obtained.

Added to 500 ml of this supernatant is an amount of sodium acetate such that a final concentration of 4% of sodium acetate is obtained. The suspension is stirred for 30 minutes at ambient temperature. Then, an amount of ethanol so as to obtain a final concentration of ethanol of 50% is added. The suspension is then stirred at ambient temperature for 30 min, and then stored without stirring overnight at +4° C.

After centrifugation at 15 000 g for 30 min, the supernatant is harvested. Sodium acetate and ethanol are added to this supernatant so as to obtain a final concentration of 4% of sodium acetate and 85% of ethanol. The suspension is stirred for 30 min at ambient temperature, and then stored without stirring overnight at 4° C. After centrifugation at 15 000 g for 30 min, the pellet is harvested.

The pellet thus obtained is taken up with 100 ml of ultrafiltered water (5-fold concentration with respect to the volume of culture supernatant centrifuged). After magnetic stirring at ambient temperature until the pellet has completely dissolved, the suspension obtained is dialyzed against 2 liters of ultrafiltered water, with three bath changes during the day, at ambient temperature, followed by an overnight step at 4° C. Tris and $MgCl_2$ are then added to the suspension thus obtained in order to obtain a final concentration of Tris of 50 mM and of $MgCl_2$ of 1 mM. This solution is incubated at 37° C. in the presence of benzonase (final concentration of 5 U/ml) with stirring. After incubation for 3 hours, benzonase is added at a final concentration of 5 U/ml and the incubation is continued for 3 hours.

An aqueous solution of pronase at 10 mg/ml is added so as to obtain a final concentration of 4 U/ml, supplemented with $CaCl_2$ at a final concentration of 1 mM. This step is then incubated for 15 hours at 37° C. If a visible cloudiness/opalescence appears, centrifugation at 8000 g for 30 min is carried out.

A 30 kDa ultrafiltration is carried out in order to remove the protein and nucleic acid fragments, under the following conditions: $H_2O$: 10 volumes; then 20 mM Tris, pH 7.5: 3 volumes.

The volume of retentate remains constant during the ultrafiltration and obtaining of a very slightly colored, clear solution.

If the retentate obtained exhibits any cloudiness/opalescence, the latter is removed by centrifugation at 8000 g for 30 min.

An ion exchange chromatography step is then carried out in order to complete the removal of the residual materials, in particular teichoic acid (TA) and lipoteichoic acid (LTA), under the following conditions: Q sepharose HP gel; 20 ml Hi Trap Q HP column; equilibration buffer: 20 mM Tris, pH 7.5; flow rate: 2 ml/min; sample injected in equilibration buffer. The equivalent of 125 ml of culture supernatant per 20 ml of gel is injected; elution:

20 mM Tris, pH 7.5: 5 column volumes gradient of 20 mM Tris, pH 7.5, 0-0.5 M NaCl: 20 column volumes 20 mM Tris, 0.5 M NaCl, pH 7.5: 5 column volumes 20 mM Tris, 1 M NaCl, pH 7.5: 5 column volumes 20 mM Tris, pH 7.5: 5 column volumes.

The elution is monitored by measuring the absorbance at 206 and 280 nm. A CZE analysis makes it possible to identify the various constituents eluted during the chromatography.

We were thus able to determine that the CP8 polysaccharide is eluted at a concentration of NaCl of between 0.2 M and 0.3 M. Under the chromatographic conditions used, said polysaccharide is clearly separated from the residual materials, the amount of which is tiny, after this chromatography step; in particular teichoic acid, which is eluted between 0.36 M and 0.48 M of NaCl, and lipoteichoic acid, which is eluted between 0.74 M and 0.86 M of NaCl.

The fractions containing the CP8 are combined and dialyzed at +4° C. against 20 volumes of a 0.5 M aqueous NaCl solution (2-3 baths) and then against 20 volumes (3-4 baths) of ultrafiltered water. The step at a high NaCl concentration enables effective removal of the Tris.

The product thus purified is freeze-dried and conserved at −20° C.

The results obtained are reported in Table 7 below.

TABLE 7

|  | CP8 assay | O-acetyl (CP by weight of powder) | | O-acetyl (CP CE assay) Analytical method | | proteins | DNA |
| --- | --- | --- | --- | --- | --- | --- | --- |
|  | CZE | Colorimetry | | | | Micro BCA direct | Picogreen |
|  | | | | Units | | | |
|  | % relative to the weight of powder | mmol/ mg CP | mol/ mol UR | mmol/ mg CP | mol/ mol UR | % W/W relative to the weight of powder | % W/W relative to the weight of powder |
| Becker (P005) pellet liquid M0/M1 | 71% | 0.93 | 0.61 | 1.31 | 0.86 | 2.2% | nd |
| CYL770 (P006) supernatant liquid M0/M1 | 85% | 1.03 | 0.68 | 1.22 | 0.80 | 0.5% | <0.1% |
| CYL770 (P007) supernatant TSB/TSB | 62% | 1.08 | 0.71 | 1.75 | 1.14 | 3.5% | nd | nd = not determined

Example 4

Culturing the *Staphylococcus aureus* Reynolds Type 5 Strain in a 30 Liter Fermenter 4.1—Culture on BTS Medium+NaCl The frozen Reynolds strain material prepared by the first method of point 2.1 is inoculated in a proportion of 0.5% by volume into two 2 l baffled Erlenmeyer flasks (E1 and E2) each containing 200 ml of tryptic soy broth supplemented with NaCl (55 g/l). The Erlenmeyer flasks are incubated at 37° C. for 5±1 hours (E1) or 48 hours (E2) with shaking at 175 rpm.

The 30 liter Braun fermenter containing 20 liters of the same medium is inoculated with 70 ml of preculture (E1) estimated at ~$1.38 \times 10^{11}$ CFU (~5 h of culture and final $OD_{600nm}$ in the Erlenmeyer flask close to 4). The culturing is carried out under the following conditions: temperature: 37° C.; culture period: 48±2 hours; pH regulated at 6.50 with 25% $NH_4OH$ and 10% $H_3PO_4$; 30% $PO_2$ (regulation in cascade: agitation 20 to 80%, air from 20 (1 vvm) to 60% (3 vvm), oxygen enrichment from 0 to 100%); pressure: 100 mbar; antifoaming regulation with $\frac{1}{50}^{th}$ struktol.

The culture is monitored during the first hours by taking regular samples, and also at 20±2 hours of culture, 24±2 hours of culture, and 42±2 hours of culture in order to verify the OD at 600 nm; the dry weight is determined; the viability is determined; the morphology is observed; glucose is assayed; acetate is assayed and the polysaccharide productivity is determined by means of the ELISA assay on 6 pellets of OD=50, after 4±2 hours, 18±2 hours, 24±3 hours, 44±3 hours and 48±2 hours of culture.

The cells are harvested after 48±2 hours of culture in 1 l centrifugation buckets (12 buckets/20 l of culture) and centrifuged for 20 minutes at 7000 g at 4° C. The wet weight is determined after removal of the supernatant. The pellets are conserved at ≤−20° C. until the step consisting of microorganism inactivation with phenol/ethanol, and then recovery and purification of the T5 polysaccharide according to the method of Example 2.

The second Erlenmeyer flask (E2) is monitored over 48 hours in order to follow the productivity of the CP5 capsule at 10 h, 24 h and 48 h of culture.

4.2-Culturing on Poutrel Medium

The frozen material of the *Staphylocoque aureus* Reynolds type 5 strain prepared according to the first method described in point 2.1 is inoculated in a proportion of 1% by volume into two 2 liter baffled Erlenmeyer flasks (E1 and E2) each containing 200 ml of Poutrel medium. The Erlenmeyer flasks are incubated at 37° C. at 175 rpm for 16±2 hours. The precultures are pooled and used to inoculate the fermenter. The culturing in a 30 l B. Braun fermenter containing 20 l of Poutrel medium is carried out under the following conditions: temperature: 37° C.; culture period: 48±2 hours; pH regulated at 6.50 with 25% $NH_4OH$ and 10% $H_3PO_4$; 30% $PO_2$ (regulation in cascade: 20 to 80% agitation, air from 20 (1 vvm) to 60% (3 vvm), oxygen enrichment from 0 to 100%); pressure: 100 mbar; antifoaming regulation with $\frac{1}{50}^{th}$ struktol.

The culture is monitored during the first hours and also at 24±2 hours of culture and 30±2 hours of culture, by taking samples in order to verify the OD at 600 nm; the dry weight is determined; the viability is determined; the morphology is observed; glucose is assayed; acetate is assayed, free amino acids are assayed and the polysaccharide productivity is determined by means of the ELISA assay.

The cells are harvested after 48±2 hours of culture.

2 l of the harvest are harvested in a 2 l Schott flask and treated with phenol/ethanol (v/v) at a final concentration of 2% (V/V). This mixture is stirred at 6 h±1 hours at 22° C.±3° C. After the supernatant has been removed from the rest of the culture, the bacterial pellets are taken up with a minimum volume of PBS buffer and then autoclaved in order to inactivate and recover the polysaccharide, according to the method described in Example 2 above.

The rest of the culture is harvested in 1 l centrifugation buckets (12 buckets/18 l of culture) and centrifuged for 20 minutes at 7000 g at 4° C. The wet weight is determined after removal of the supernatant. 2 liters of supernatant are conserved at ≤−20° C. after 0.45 μm filtration and autoclaving at 121° C. for 55 minutes.

The 12 pellets are resuspended in a minimum volume of PBS buffer (approximately 650 ml) using an ultraturax. The suspensions are pooled, homogenized and dispensed equally into three 500 ml Schott flasks (approximately 300 ml/Schott flask) before autoclaving at 121° C. for 55 min. The autoclaved suspensions are then pooled and the polysaccharide is recovered according to the protocol described in Example 2 above.

4.3—Culture on Columbia Medium+NaCl

Frozen *Staphylococcus aureus* Reynolds type 5 material prepared according to the first method of point 2.1 is inoculated in a proportion of 1% by volume into two 2 l baffled Erlenmeyer flasks each containing 200 ml of columbia medium+20 g/l of NaCl (Difco ref. 2944201). The Erlenmeyer flasks are incubated at 37° C. for 24±2 hours with shaking at 175 rpm. After 24±2 hours, the precultures are pooled and used to inoculate the fermenter. The culturing in the 30 l B. Braun fermenter containing 20 l of the same medium is carried out under the following conditions: temperature: 37° C.; culture period: 24±2 hours; pH regulated at 7.00 with 25% $NH_4OH$ and 10% $H_3PO_4$; 30% $PO_2$ (regulation in cascade: 20 to 80% agitation, air from 20 (1 vvm) to 60% (3 vvm), oxygen enrichment from 0 to 100%); pressure: 100 mbar; antifoaming regulation with $1/50^{th}$ struktol.

The culture is monitored regularly by taking regular samples in order to verify the OD at 600 nm; the dry weight is determined; the viability is determined; the morphology is observed; glucose is assayed; acetate is assayed and the polysaccharide productivity is determined by means of the ELISA assay.

The cells are then harvested at 24±2 hours of culture. The final culture is transferred into 1 l centrifugation buckets (12 buckets/20 l of culture) and centrifuged for 20 minutes at 7000 g at 4° C. The wet weight is determined after removal of the supernatant. After centrifugation, the 12 pellets are resuspended, using an ultraturax, in a minimum volume of PBS buffer of between 1 and 1.2 l. The suspensions are pooled, homogenized and distributed equally into 500 ml Schott flasks, and then autoclaved at 121° C. for 55 minutes. The autoclaved suspensions are then pooled and the polysaccharide is recovered according to the protocol described in Example 2 above.

4.4—Culture on Medium M1

Frozen *Staphylococcus aureus* Reynolds type 5 material prepared according to the first method described in point 2.1 above is taken up in 1C PBS buffer in a proportion of 1 ml of frozen material per 9 ml of buffer, so as to seed approximately 10 dishes of agar medium M0 in a proportion of 150 µl/dish.

The dishes are incubated at 37° C. for 15 to 18 hours. After incubation for 15-18 h at 37° C., the layers formed are scraped up before being resuspended in medium M1 in order to inoculate two Erlenmeyer flasks of identical composition (200 ml/2 l—E1 and E2) so as to have an initial $OD_{600nm}$ close to 0.2 in each Erlenmeyer flask. The Erlenmeyer flasks are incubated at 37° C. with shaking at 175 rpm for approximately 5 h (culture in exponential phase, E1) or 72 hours (E2).

Part of the E1 culture ($OD_{600nm}$, close to 3) is used to inoculate the 30 l B. Braun fermenter containing 20 l of medium M1 so as to have an initial $OD_{600nm}$, close to 0.02.

The culturing is carried out under the following conditions: temperature: 37° C.; culture period: 72±4 hours; pH regulated at 6.50 with 25% $NH_4OH$ and 10% $H_3PO_4$; 30% $PO_2$ (regulation in cascade: 20 to 80% agitation, air from 20 (1 vvm) to 60% (3 vvm), oxygen enrichment from 0 to 100%); pressure: 100 mbar; antifoaming regulation with $1/50^{th}$ struktol.

1 l of culture is then harvested in centrifugation buckets and centrifuged for 20 minutes at 7000 g at 4° C. in order to determine the wet weight after removal of the supernatant. The pellets are conserved at −20° C.

The rest of the culture is harvested in a 50 l Nalgen and inactivated with phenol/ethanol (final concentration of 2% V/V) and the polysaccharide is recovered according to the protocol described in Example 2 above.

All the results obtained are reported in Table 8 below.

TABLE 8

| Media | Columbia + NaCl | Poutrel | BTS + NaCl | M1 |
| --- | --- | --- | --- | --- |
| Final OD | 21 | 16 | 17 | 16 |
| [CP5] extraction lysostaphin | nd | 6.6 mg/l | nd | 130 mg/l |
| [CP5] extraction autoclave | 0.2 mg/l | 3.7 mg/l | 3.5 mg/l | 40 mg/l |
| Specific yield (µg/OD) | 0.01 | 0.23 | 0.21 | 2.5 |

What is claimed is:

1. A method for the production of a *Staphylococcus aureus* serotype T5 or T8 capsular polysaccharide, comprising:
   (a) culturing a *Staphylococcus aureus* strain that produces a serotype T5 or T8 capsular polysaccharide on a culture medium comprising per liter of culture medium:
      (i) 52.5 to 200 g of plant peptone or 65 to 85 g yeast extract,
      (ii) 0 to 82.5 g of NaCl,
      (iii) 0 to 15 g of a magnesium salt selected from the group consisting of $MgSO_4$ and $MgCl_2$, and
      (iv) 0 to 7 g of sugar, the pH of which is within a range of values of from 6.3 to 6.7,
   (b) inactivating the culture thus produced, and
   (c) recovering the capsular polysaccharide.

2. The method according to claim 1, wherein the plant peptone is wheat peptone.

3. The method according to claim 1, wherein the culture medium comprises per liter of culture medium:
   (i) 52.5 to 100 g of wheat peptone,
   (ii) 5 to 82.5 g of NaCl,
   (iii) 0.01 to 15 g of a magnesium salt selected from the group consisting of $MgSO_4$ and $MgCl_2$, and
   (iv) 0.25 to 7 g of sugar, the pH of which is within a range of values of from 6.3 to 6.7.

4. The method according to claim 3, wherein the culture medium comprises per liter of culture medium:
   (i) 93 g of wheat peptone,
   (ii) 41 g of NaCl,
   (iii) 15 g of $MgCl_2$, $6H_2O$, and
   (iv) 0.25 g of D-Glucose $H_2O$, the pH of which is within a range of values of from 6.3 to 6.7.

5. The method according to claim 1, wherein the culture medium comprises per liter of culture medium:
   (i) 75 g of yeast extract,
   (ii) 0 to 82.5 g of NaCl,
   (iii) 0 to 15 g of a magnesium salt selected from the group consisting of $MgSO_4$ and $MgCl_2$, and
   (iv) 0 to 7 g of sugar, the pH of which is within a range of values of from 6.3 to 6.7.

* * * * *